United States Patent [19]
Shamshoum et al.

[11] Patent Number: 6,107,501
[45] Date of Patent: Aug. 22, 2000

[54] SYNTHESIS OF METALLOCENES AND ENRICHMENT OF THEIR RAC ISOMER

[75] Inventors: Edwar Shoukri Shamshoum, Houston; Christopher G. Bauch, Seabrook, both of Tex.

[73] Assignee: Fina Technology, Inc., Dallas, Tex.

[21] Appl. No.: 08/790,783

[22] Filed: Jan. 30, 1997

[51] Int. Cl.[7] ............................ C07F 17/00; C07F 7/00
[52] U.S. Cl. ........................ 556/11; 556/53; 502/103; 502/117; 526/160; 526/943
[58] Field of Search ............... 556/11, 53; 502/103, 502/117; 526/160, 943

[56] References Cited

U.S. PATENT DOCUMENTS

| | | | |
|---|---|---|---|
| 5,117,020 | 5/1992 | Razavi | 556/43 |
| 5,145,819 | 9/1992 | Winter et al. | 502/117 |
| 5,239,022 | 8/1993 | Winter et al. | 556/127 |
| 5,243,001 | 9/1993 | Winter et al. | 526/127 |
| 5,276,208 | 1/1994 | Winter et al. | 556/53 |
| 5,278,264 | 1/1994 | Spalek et al. | 526/127 |
| 5,302,733 | 4/1994 | Diefenbach et al. | 556/11 |
| 5,304,614 | 4/1994 | Winter et al. | 526/127 |
| 5,328,969 | 7/1994 | Winter et al. | 526/127 |
| 5,329,033 | 7/1994 | Spalek et al. | 556/53 |
| 5,374,752 | 12/1994 | Winter et al. | 556/11 |
| 5,441,920 | 8/1995 | Wellborn | 502/103 |
| 5,455,365 | 10/1995 | Winter et al. | 556/7 |
| 5,455,366 | 10/1995 | Rohrmann et al. | 556/8 |
| 5,616,747 | 4/1997 | Rohrmann et al. | 556/11 |
| 5,780,660 | 7/1998 | Lin et al. | 556/11 |

*Primary Examiner*—Porfirio Nazario-Gonzalez
*Attorney, Agent, or Firm*—Evan K. Butts; Jim D. Wheelington

[57] ABSTRACT

Provided is method of synthesizing stereorigid metallocene having chiral center and enriching its rac isomer content; comprising steps of:

a) selecting desired cyclopentadienyl ring-containing compound capable of forming metallocene with chiral center and dissolving compound in suitable solvent;

b) contacting mixture of a), under suitable conditions of mixing and temperature for sufficient time to react, with suitable alkyl alkali metal compound;

c) dissolving solid created in b) with sufficient suitable solvent;

d) contacting solution created in c) with suitable halogenated compound with which bridge between two cyclopentadienyl ring-containing compounds may be formed, under suitable conditions of mixing and temperature for sufficient time to react;

e) removing solvent, and, optionally, removing residual starting cyclopentadienyl ring-containing compound;

f) dissolving solid created in e) in suitable solvent and contacting with suitable alkyl alkali metal compound under suitable conditions of temperature and mixing for a sufficient time to react;

g) removing solvent, and, optionally, removing residual starting cyclopentadienyl ring-containing compound;

h) slurrying or suspending solid created in g) with sufficient suitable solvent;

i) contacting slurry or suspension of h) with sufficient suitable metal tetrahalide under suitable conditions of temperature and mixing for a sufficient time to react;

j) removing residual alkali halide from solid created in i);

k) removing solvent from solid of j);

l) enriching rac metallocene isomer by suspending solid of k) in suitable solvent in suitable amount under suitable conditions of temperature and mixing for time sufficient to solvate non-rac isomers;

m) removing supernatant;

n) repeating steps l) and m) with diminishing amounts of suitable solvent as necessary to attain desired enrichment level; and o) recovering desired product.

9 Claims, 1 Drawing Sheet meso rac

2

SYNTHESIS OF METALLOCENES AND ENRICHMENT OF THEIR RAC ISOMER

FIELD OF THE INVENTION

This invention relates to means for synthesis of and enrichment or isolation of different enantiomers of metallocene molecules. Such molecules are useful in polymerization catalysis, particularly for olefin polymerization, and vary in their tacticity differentiation of polymers produced by their catalysis.

BACKGROUND OF THE INVENTION

It is known in the art that metallocenes, notably those of Groups 3–6, particularly those including the Group 4 metals of the Periodic Table of the Elements, become active polymerization catalysts in combination with appropriate cocatalyst and are particularly useful in production of polyolefins, particularly when α-olefins are contacted with such catalyst systems. When the structure of the metallocene is rigidified by a bridging ligand between the aromatic rings, hetero atom, other non-halide or small-group alkyl radical, or combinations thereof, chiral centers arise and it becomes possible to form both rac and meso forms of numerous metallocene-type molecules. With this chirality, the potential for production of tacticity specific polymers becomes possible. This may be accomplished particularly by polymerization of olefins, particularly alpha-olefins, having at least three carbon atoms. Therefore, it is possible to create tacticity differentiated polymers by polymerizing propylene, longer-chain olefins, or combinations thereof.

With bridged metallocenes, it is possible to create both the rac and meso forms of the catalytically active molecule. In polymerization of α-olefins only the rac isomer is isospecific and therefore able to produce isotactic polymer. To accomplish this it is necessary to isolate the rac isomer or somehow produce only that isomer.

Razavi describes, in U.S. Pat. No. 5,158,920, a process for producing stereospecific polymers. This is accomplished by deprotonation of a cyclopentadiene in a polar solvent to form a solution of the corresponding anionic species followed by steps to create a metallocene from the anionic species.

Winter et al. describe, in U.S. Pat. No. 5,145,819, syntheses of various metallocenes followed by enrichment of the rac isomer with enrichment to levels of more than 17:1 and more than 15:1 rac:meso forms. Two enrichment schemes are reported to obtain these respective results. One involves repetition of a cumbersome scheme of 1) stirring of the racemic metallocene mixture with n-pentane and drying, 2) suspending the resulting solid in THF, and 3) filtering off the suspension. The second involves a toluene extraction of a residue resulting from a late synthesis evaporation step followed by evaporation, followed by THF extraction, which is then followed by recrystallization from toluene.

Kaminsky reports, in U.S. Pat. No. 4,769,510, a synthesis of metallocenes in which temperatures at particular points in the process are carefully controlled, and maintained quite low, to finally attain an enriched mixture with greater than predicted rac form concentration.

Others have worked to reliably produce differentiated tacticity polyolefins and the catalysts enabling such production. The methods described to date have shortcomings of low enrichment, cumbersome multi-step or repetitive processes. We provide means for accomplishing the goal of isolating rac bridged metallocene-type molecules for production of isospecific polymer, particularly poly-α-olefins. Our method uses a simple, commercially economic repetition of a simple toluene wash to attain enrichment concentrations of rac:meso forms in excess of about 20:1.

DETAILED DESCRIPTION

Figure 1:
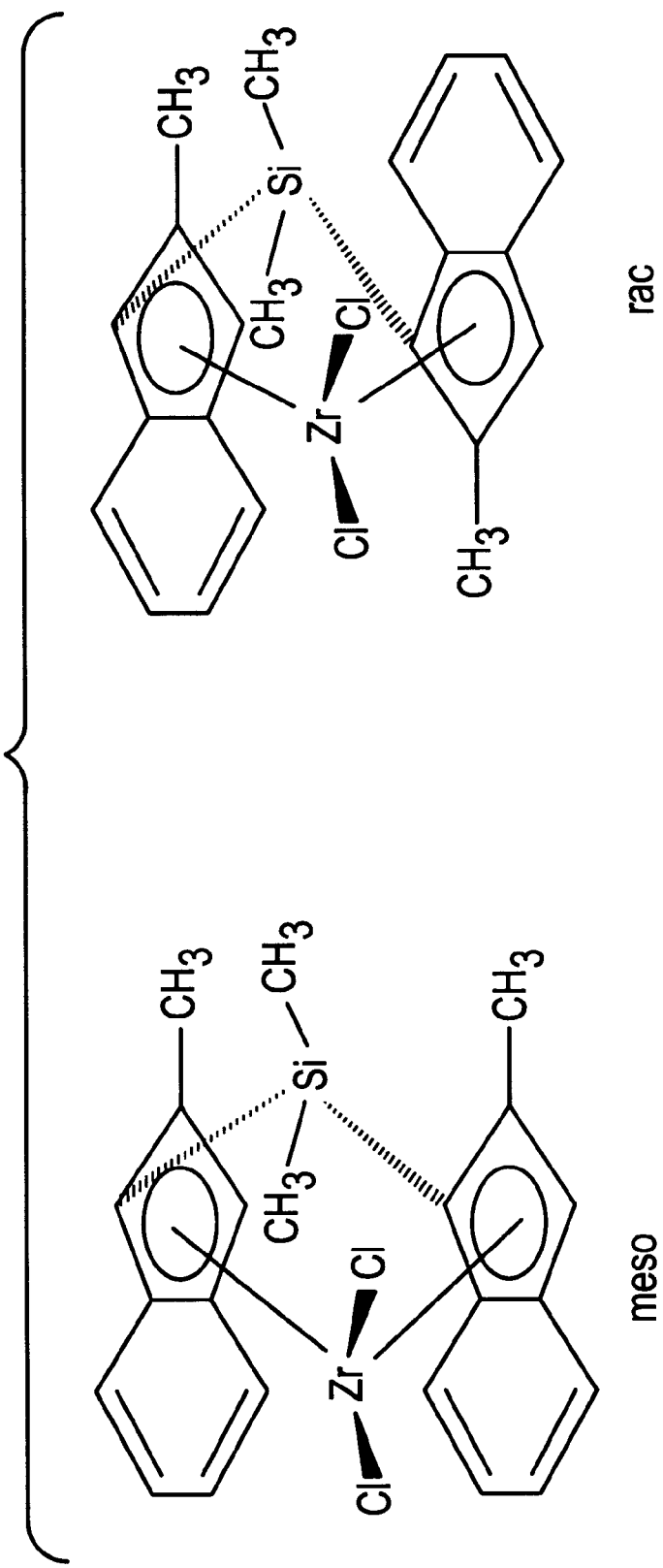
FIG. 1 provides schematic drawings of the rac- and meso-forms of $Me_2Si(2-Me-Ind)_2ZrCl_2$, one useful stereospecific metallocene catalyst.

Our invention provides means of synthesizing stereorigid metallocenes having chiral centers and enriching the metallocene's rac isomer content; comprising steps of:

a) selecting desired cyclopentadienyl ring-containing compound capable of forming metallocene with chiral center and dissolving compound in suitable solvent, such as most ethers; protonated solvents, carbonyls, and other alkali metal-reactive solvents should be avoided;

b) contacting mixture of a) under suitable conditions of mixing and temperature for sufficient time to react, with suitable alkyl alkali metal compound;

c) dissolving solid created in b) with sufficient suitable solvent;

d) contacting solution created in c) with suitable halogenated compound, particularly dihalogenated aliphatics, with which bridge between two cyclopentadienyl ring-containing compounds may be formed, under suitable conditions of mixing and temperature for sufficient time to react;

e) removing solvent, and, optionally, removing residual starting cyclopentadienyl ring-containing compound;

f) dissolving solid created in e) in suitable solvent and contacting with suitable alkyl alkali metal compound under suitable conditions of temperature and mixing for a sufficient time to react;

g) removing solvent, and, optionally, removing residual starting cyclopentadienyl ring-containing compound;

h) slurrying or suspending solid created in g) with sufficient suitable solvent;

i) contacting slurry or suspension of h) with sufficient suitable metal tetrahalide under suitable conditions of temperature and mixing for a sufficient time to react;

j) removing residual alkali halide from solid created in i);

k) removing solvent from solid of j);

l) enriching rac metallocene isomer by suspending solid of k) in suitable solvent in suitable amount under suitable conditions of temperature and mixing for time sufficient to solvate non-rac isomers;

m) removing supernatant;

n) repeating steps l) and m) with diminishing amounts of suitable solvent as necessary to attain desired enrichment level; and o) recovering desired product.

Another embodiment provides means of synthesizing stereorigid metallocenes having chiral centers, comprising steps of:

a) selecting desired cyclopentadienyl ring-containing compound capable of forming metallocene with chiral center and dissolving compound in suitable ether;

b) contacting mixture of a), under suitable conditions of mixing and temperature for sufficient time to react, with suitable alkyl alkali metal compound;

c) dissolving solid created in b) with sufficient suitable solvent;

d) contacting solution created in c) with suitable halogenated compound with which bridge between two cyclopentadienyl ring-containing compounds may be formed, under suitable conditions of mixing and temperature for sufficient time to react;

e) removing solvent, and, optionally, removing residual starting cyclopentadienyl ring-containing compound;

f) dissolving solid created in e) in suitable solvent and contacting with suitable alkyl alkali metal compound under suitable conditions of temperature and mixing for a sufficient time to react;

g) removing solvent, and, optionally, removing residual starting cyclopentadienyl ring-containing compound;

h) slurrying or suspending solid created in g) with sufficient suitable solvent;

i) contacting slurry or suspension of h) with sufficient suitable metal tetrahalide under suitable conditions of temperature and mixing for a sufficient time to react;

j) removing residual alkali halide from solid created in i);

k) removing solvent from solid of j) and recovering desired product.

A further embodiment provides method of enrichment, isolation, purification, or combinations thereof of rac isomer of metallocene; comprising steps of:

a) selecting stereorigid metallocene having chiral center whose rac isomer content is desired to be enriched, isolated, purified, or combinations thereof;

b) suspending metallocene of a) in suitable solvent in suitable amount under suitable conditions of temperature and mixing for time sufficient to solvate non-rac isomers;

c) removing supernatant;

d) repeating steps b) and c) with diminishing amounts of suitable solvent as necessary to attain desired enrichment, isolation, purification, or combinations thereof level; and e) recovering desired product.

Notable benefits result from use of these processes. First, in the metallocene synthesis, the solvent used is not dichloromethane or any other halogenated solvent. This by itself will help to limit side reactions with the halogenated alkyls, including dichloromethane, thus producing a more pure product. Second, this synthesis and the separation, of rac- and meso-forms, or enrichment may be conducted at higher temperatures than those previously found in the literature. Being able to conduct such steps at higher temperatures, particularly ambient or near-room temperatures, makes these embodiments more commercially viable and desirable for large-scale production and makes the process easier to control.

Each of these processes will be useful for metallocenes of different metallic elements. Particular benefits will accrue with metals of Groups 3–6 of the Periodic Table of the Elements. Particularly useful results will be found with the metals of Group 4, especially titanium, zirconium and hafnium with the latter two being more preferred.

While ethers, particularly the dialkyl, mixed alkyl ethers, and their combinations are preferred in the initial dissolution step other ethers are useful also.

Useful stereo rigid metallocenes may be created from substituted cyclopentadienyl rings, where it is possible that substituents may become fused ring arrangements such as for example indenyl or fluorenyl ring structures, heteroatoms, or combinations thereof. Stereorigidity derives from a bridging group "locking out" free rotation of the rings or heteroatoms. Such bridges may usefully be from one to about four atoms comprising the actual bridge such that radicals containing carbon, silicon, germanium, or combinations thereof which form the actual bridge are continuous between the bridged rings or other groups. These bridges may be of alkylene, silylene, silyl, alkyl, germyl, germylene radicals or combinations thereof. Clearly, such bridging groups may have pendant atoms which are not part of the actual bridge formation; these do not enter into the number counted as the bridge. A point of interest is that those metallocenes having alkyl bridges are generally more stable at higher temperatures than are those with silyl bridges.

Useful solvents include the alkanes for salvation of the early stage reactions of the syntheses. Halogenated solvents are useful for removing some impurities, particularly the alkali halides created in the synthetic scheme; they are less preferred during actual reactions as they may promote unneeded and interfering side reactions. Solvents useful for solvating the intermediates in the reaction include aromatics and furans. Preferably, these will be saturated to a high degree to prevent other side reactions. Useful examples include non-polar and minimally polar solvents such as hydrocarbons or very slightly polar solvents such as a mixture of toluene and non-polar hydrocarbons, ethyl benzene and other similarly sparingly polar solvents.

Solvents useful for the washing of the final products and enrichment of the desired stereoisomer concentration include solvents which are generally non-coordinating and somewhat polar. While toluene is an excellent choice, other solvents including xylenes, preferably meta-xylene, more preferably ortho-xylene, benzene, ethyl benzene, cumene, and others will perform beneficially in this function. Should it be desirable to employ a minimally or non-coordinating solvent with a somewhat higher degree of polarity than toluene, this may be accomplished neatly by tempering the solvent's polarity with a different non-polar solvent. Hexane is useful as a tempering agent in such instances. Since toluene is such a useful choice in this separation, it is useful, when using another solvent, to temper its polarity with non-polar solvent to the extent that the system polarity approximates that of toluene.

Conversely, it may occasionally be desirable to accomplish the enrichment or separation with toluene but polarity lower than that of toluene would be useful. In such an instance, the polarity of toluene may be tempered lower by addition of a non-polar solvent such as hexane to attain an overal effective solvent system polarity which is lower than the polarity of toluene.

With this separation/enrichment scheme there is a generally inverse relationship between temperature and amount of solvent needed. For example, such separation may be accomplished at elevated temperature with comparatively little generally non-coordinating somewhat polar solvent. Conversely, the enrichment may be accomplished at low temperatures with a high concentration of the solvent of choice, notably toluene. As a general consideration, the separation may be conducted within a temperature range between which the desired species are solvated and decomposing. This will generally be practical between about −25° C. and about 80° C.

Preferred products will be those which are bis-indenyl or bis-fluorenyl metallocenes with $Me_2Si(2-Me-Ind)_2ZrCl_2$ or its alkylated analogue being a preferred species which has proven useful in polymerization of isotactic poly-α-olefins of greater than two carbon atoms.

EXAMPLES

Example 1

Synthesis of $Me_2Si(2\text{-}Me\text{-}Ind)_2ZrCl_2$

By dropwise addition 59 ml of 2.5M BuLi (94.4 mmole), in hexanes, was added to a 0° C. solution of 2-methyl-indene (12.1 g, 93.1 mmole) in 150 ml $Et_2O$. The reaction mixture was then warmed to 40° C. for one hour. The mixture was then cooled to 0° C. Sufficient THF to dissolve the solid, about 15 ml, was added. A solution of $Me_2SiCl_2$ (5.6 ml, 46 mmole) in 25 ml THF was added dropwise. The reaction mixture was allowed to rise to room temperature and stir overnight. The solvent was then recovered under vacuum; the residue was extracted with hexane and filtered through Celite 503 as obtained from J. T. Baker through VWR Scientific in Sugarland, Tex. A bed of approximately 2.5 cm (1 inch) thickness was used; generally it is useful to employ a bed of sufficient thickness to prevent LiCl formed by reaction from reaching the funnel frit. The solvent was removed from the filtrate under vacuum to yield an off-white semi-solid containing about 9% (by GC) of 2-Me-Indene. The 2-Me-Indene was removed by vacuum distillation.

The $Me_2Si(2\text{-}Me\text{-}Ind)_2$ (7.6 g, 24 mmole) was dissolved in 180 ml THF and 30 ml of BuLi (1.6M in hexanes, 48 mmole) was added dropwise over 30 minutes. This solution was then warmed to 40° C. for two hours. The solvent was removed under vacuum to yield a sticky yellow solid which was then washed twice with hexane and dried under vacuum to obtain the dianion which was then slurried in 100 ml toluene. $ZrCl_4$ was added as a toluene slurry at room temperature and the resulting slurry was stirred overnight. The supernatant liquid was removed by cannula and the solid dried under vacuum. To remove the resulting LiCl, the solid was dissolved in $CH_2Cl_2$ and filtered through Celite. The solvent was removed under reduced pressure yielding a yellow solid which was then washed with hexane and dried under vacuum. Yield was about 77% with a rac:meso ratio=1.3 (insoluble):0.6 (soluble).

A notable benefit of this synthesis is that we do not use chlorinated solvents and do not cool the reaction flask to low temperatures. Our synthesis may be run using other hydrocarbon solvents including heptane and hexane at temperatures ranging from about −20° C. to about 30° C. It is preferable to cool the reaction flask when using aromatic hydrocarbon solvents including toluene in light of the greater solubility of the reactants in such solvents as compared to aliphatic hydrocarbon solvent candidates. Other published syntheses require cooling the dianion to −78° C. in dichloromethane prior to addition of $ZrCl_4$. Since hydrocarbon solvents are relatively inert compared to dichloromethane, possible interfering and yield-reducing side reactions with solvent are eliminated.

Isolation of rac $Me_2Si(2\text{-}Me\text{-}Ind)_2ZrCl_2$

Our method of purification for $Me_2Si(2\text{-}Me\text{-}Ind)_2ZrCl_2$ involves suspending the solid in toluene at a ratio of approximately 10:1 with respect to the solid (ml:g) and heating the suspension to 50° C. The suspension is stirred for between about half an hour to about an hour and allowed to settle at room temperature. The supernatant liquid is removed by cannula. This process is repeated with about half the amount of toluene for subsequent washes, typically about four or five times, until the desired isomeric purity, greater than about 20:1 rac:meso, is obtained. The resulting solid is then washed with hexane and dried under vacuum at about 60° C. Typically, about 80% of the rac isomer was isolated for the zirconocene by use of this method.

Example 2

The crude product contains lithium chloride which may be removed by dissolution of the metallocene in dichloromethane followed by filtration through Celite, as was done in Example 1. For this Example, the dissolution and filtration step would be performed after removal of the meso isomer to yield similar results to those obtained in Example 1.

Example 3

Other stereo rigid metallocenes capable of producing tacticity specific polymers may be produced with numerous substituted cyclopentadienyl ring structures. Generally such metallocenes which have bulky substituents will be more capable of producing differentiated tacticity polymers of lower error rate. A bis-cyclopentadienyl metal compound with a t-butyl substituent on each ring will, for example, produce a lower error rate than will a similar compound with a methyl substituent on each ring. The isolation procedure presented here, however, will still function well with these compounds.

Example 4

In general, metallocenes created with smaller metal atoms will produce tacticity differentiated polymers with lower error rates than will those created with larger diameter metal atoms. A stereo rigid titanocene, for example, will produce polyolefins with lower error rates than will the similar zirconocene or hafnocene. This is generally the case but as the olefins being polymerized become extremely large, steric considerations with the smaller diameter metal atoms may prevent reasonable activity. Similar syntheses and isolation methods for the rac isomer will be fully functional for metallocenes created from differing metals. Such metals will include those of Groups 3, 4, 5, and 6 of the Periodic Table of the Elements, preferably those of Group 4, with zirconium being the preferred member of that group.

Example 5

Metallocenes with other stereorigid bridges may also be created. Alkylene or dialkyl bridges, for example will form functional stereorigid isomers. Similar synthesis and isolation schemes, to that presented here, will provide similar results to those as demonstrated.

Example 6

Other useful stereospecific metallocenes may be produced, enriched, or combinations thereof with this scheme. This will include other 1-substituted species including 1-ethyl, 1-propyl, 1-isopropyl, 1-phenyl, and others.

Example 7

Further, successful stereospecific metallocenes which are 4-substituted will be produced, enriched, or both by this process. These will include 4-methyl, 4-ethyl, 4-propyl, 4-isopropyl, 4-phenyl, and others including bicyclic groups including napthalenyl. The 4-phenyl substituted species yields particularly useful catalysts.

Example 8

Other metallocenes which are polyalkyl substituted are also useful. These will include species substituted at the 2, 3, and 5 positions including substitutions with radicals such as propyl, ethyl, methyl, and their combinations. Such species may be produced, enriched, or both through t he practice of this invention.

Example 9

Other useful catalysts may be produced, enriched, or both by this process when substitutions are made on the phenyl portion of the indenyl structure. These will include substitutions at positions 4, 5, 6, or combinations thereof. Useful such substituents will include alkyl and aryl substituents such as methyl, ethyl, propyl, isopropyl, phenyl, others, and their combinations.

These examples are provided for assistance in understanding this invention and the way in which it works. They are not intended, in any fashion, to limit the invention but are, simply illustrative. Those skilled in the art will recognize, from these representative examples and the entirety of this description, modifications which have not been specifically mentioned but which are intended to be included within this invention as claimed below.

We claim:

1. Method of synthesizing stereorigid metallocene having chiral center and enriching its rac isomer content, comprising steps of:
    a) selecting desired cyclopentadienyl ring-containing compound capable of forming metallocene with chiral center and dissolving compound in solvent suitable for dissolving such compound provided that solvent is not alkali metal-reactive;
    b) contacting mixture of a), under suitable conditions of mixing and temperature for sufficient time to react, with suitably reactive alkyl alkali metal compound;
    c) dissolving solid created in b) with sufficient solvent suitable for dissolving solid;
    d) contacting solution created in c) with suitable halogenated compound with which bridge between two cyclopentadienyl ring-containing compounds may be formed, under suitable conditions of mixing and temperature for sufficient time to react;
    e) removing solvent, and, optionally, removing residual starting cyclopentadienyl ring-containing compound;
    f) dissolving solid created in e) in solvent suitable for dissolving this solid and contacting with suitable alkyl alkali metal compound under suitable conditions of temperature and mixing for a sufficient time to react;
    g) removing solvent, and, optionally, removing residual starting cyclopentadienyl ring-containing compound;
    h) slurrying or suspending solid created in g) with sufficient solvent suitable for slurrying or suspending this compound;
    i) contacting slurry or suspension of h) with sufficient suitable metal tetrahalide under suitable conditions of temperature and mixing for a sufficient time to react;
    j) removing residual alkali halide from solid created in i);
    k) removing solvent from solid of j);
    l) enriching rac metallocene isomer by suspending solid of k) in solvent suitable for solvating non-rac isomers in suitable amount under suitable conditions of temperature and mixing for time sufficient to solvate non-rac isomers;
    m) removing supernatant;
    n) repeating steps l) and m) with diminishing amounts of suitable solvent as necessary to attain desired enrichment level; and
    o) recovering desired product;
    p) providing that:
        i) steps a) through i) are conducted at temperatures greater than about −25° C. and solvent used is not dichloromethane or other halogenated solvent, and
        ii) steps j) through n) are conducted at temperatures greater than about −20° C.

2. Method of claim 1 wherein solvent suitable for dissolving solid of c) is selected from alkanes, ethers, or their combinations.

3. Method of claim 2 wherein suitably reactive alkyl alkali metal compound of b) comprises between one and about four atoms, which will make up actual bridge, of carbon, silicon, germanium, or combinations thereof.

4. Method of claim 3 wherein suitably reactive alkyl alkali metal compound of b) is butyl lithium.

5. Method of claim 3 wherein solvent, suitable for dissolving, of f) is selected from aromatics, furans, or combinations thereof.

6. Method of claim 5 wherein desired cyclopentadienyl ring-containing compound, of a), comprises indenyl or fluorenyl ring.

7. Method of claim 6 wherein solvent, suitable for solvating non-rac isomers, of l) is selected from toluene, xylenes, benzene, ethyl benzene, cumene, combination of polar solvent with a polarity-tempering agent, or combinations thereof.

8. Method of claim 7 wherein solvent, suitable for solvating non-rac isomers, of l) is toluene.

9. Method of claim 7 wherein desired product of o) is $Me_2Si(2\text{-}Me\text{-}Ind)_2ZrCl_2$.

* * * * *